(12) United States Patent  (10) Patent No.: US 6,482,213 B1
Riza  (45) Date of Patent: Nov. 19, 2002

(54) RUBBER BAND STRETCHER

(76) Inventor: Erol D. Riza, 550 Riverside Dr., Rossford, OH (US) 43460

( * ) Notice: Subject to any disclaimer, the term of this patent is extended or adjusted under 35 U.S.C. 154(b) by 140 days.

(21) Appl. No.: 09/583,118

(22) Filed: May 30, 2000

(51) Int. Cl.[7] .............................................. A61B 17/10
(52) U.S. Cl. ...................................................... 606/140
(58) Field of Search ................... 606/139–141, 606/148, 151; 40/304

(56) References Cited

U.S. PATENT DOCUMENTS

| 3,726,278 | A | * | 4/1973 | Scott ............................ 40/304 |
| 3,911,923 | A | * | 10/1975 | Yoon ........................... 128/831 |
| 4,628,915 | A | * | 12/1986 | Chaney ......................... 600/41 |
| 4,788,966 | A | * | 12/1988 | Yoon ........................... 128/831 |
| 4,921,423 | A | | 5/1990 | Kesling |
| 4,990,152 | A | | 2/1991 | Yoon |
| 5,122,149 | A | | 6/1992 | Broome |
| 5,158,563 | A | * | 10/1992 | Cosman ........................ 606/140 |
| 5,261,918 | A | | 11/1993 | Phillips et al. |
| 5,464,412 | A | | 11/1995 | Budding |
| 5,601,574 | A | * | 2/1997 | Stefanchik et al. .......... 606/139 |
| 5,643,290 | A | | 7/1997 | Clark et al. |
| 5,704,943 | A | * | 1/1998 | Yoon et al. ................... 606/139 |
| 5,716,368 | A | * | 2/1998 | de la Torre et al. ........ 112/169 |
| 5,741,273 | A | * | 4/1998 | O'Regan ........................ 606/1 |
| 5,957,936 | A | * | 9/1999 | Yoon et al. ................... 606/144 |
| 6,051,003 | A | * | 4/2000 | Chu et al. .................... 604/272 |
| 6,059,797 | A | * | 5/2000 | Mears .......................... 606/139 |
| 6,136,009 | A | * | 10/2000 | Mears .......................... 606/140 |
| 6,203,553 | B1 | * | 3/2001 | Robertson et al. ......... 227/175.1 |
| 6,206,893 | B1 | * | 3/2001 | Klein et al. .................. 606/139 |
| 6,280,452 | B1 | * | 8/2001 | Mears .......................... 606/139 |
| 6,325,809 | B1 | * | 12/2001 | Bryars ......................... 128/898 |
| 6,350,269 | B1 | * | 2/2002 | Shipp et al. ................. 606/143 |

OTHER PUBLICATIONS

George Percy McGown catalog for McGivney Hemorrhoid Ligator, copyright 1990, cover page, index page, and pp. 10,11.

* cited by examiner

Primary Examiner—David O. Reip
Assistant Examiner—Daniel Jacob Davis
(74) Attorney, Agent, or Firm—FMCH, Schaffer, Schaub & Porcello Co., L.P.A.

(57) ABSTRACT

An apparatus including a serrated cone for interoperation with a loader. The cone includes a conical ramp portion, a cylindrical base portion, and at least one fin slot. The ramp portion defines a cone ramp surface and has a large diameter end and a small diameter end. The base portion extends longitudinally from the large diameter end of the ramp portion and has a radially outer surface. The fin slot is defined in the cone ramp surface and the radially outer surface of the base portion. The loader includes a plunger and a glider. The plunger has a fin for urging the elastomeric band along the ramp portion. The glider has a surface for engaging the elastomeric band and urging the elastomeric band over the base portion. The glider is moveably related to the plunger.

17 Claims, 11 Drawing Sheets

RUBBER BAND STRETCHER

TECHNICAL FIELD

This invention relates to a device for stretching rubber bands or other elastomeric bands. More specifically, the invention of this application is a mechanical instrument for efficiently stretching and moving a ligature ring, for example, onto the end of a McGivney Hemorrhoidal Ligator or other suitable surgical instrument.

BACKGROUND OF THE INVENTION

This invention is intended to be used in conjunction with gastroenterology and proctology procedures like hemorrhoidectomy. The nature of those procedures and the techniques for performing hemorrhoidectomy are well documented. Hemorrhoidectomy is the mainstream of proctologic surgeries. Hemorrhoidectomy using a ligature ring and McGivney Hemorrhoidal Ligator (MHL) is one of the surgical techniques commonly used. In the procedure, the operator seeks to ligate the hemorrhoidal tissue with application of a ligature ring to the base of the hemorrhoidal tissue. Ligature rings are elastomeric rings which can be made of rubber.

In the prior art the ligature rings are loaded to the end of the MHL by moving or rolling the ligature ring up a loading cone, typically by gloved hands, and onto a MHL. The hemorrhoid is pulled into the cavity of the MHL instrument with a grasping device or by suction. The ligature ring is released from the MHL around the base of the hemorrhoid. Constriction of the base of the hemorrhoid begins a natural process which results in an eventual sloughing of the hemorrhoid.

Difficulty of rolling these ligature rings with gloved hands has been a practical problem for surgeons and surgical assistants. Rolling the ligature ring up a loading cone gradually becomes difficult as the ligature rings becomes distended and thinned and gloves are caught in the rolling ligature rings. This can cause the gloves to pinch or break or the ligature rings to break.

SUMMARY OF THE INVENTION

The apparatus of the invention includes a serrated cone and a loader. The cone includes a conical ramp portion, a cylindrical base portion, and at least one fin slot. The ramp portion defines a cone ramp surface and has a large diameter end and a small diameter end. The base portion extends longitudinally from the large diameter end of the ramp portion and has a radially outer surface. The fin slot is defined in the cone ramp surface and the radially outer surface of the base portion. The loader includes a plunger and a glider. The plunger has a fin for urging the elastomeric band along the ramp portion. The glider has a surface for engaging the elastomeric band and urging the elastomeric band over the base portion. The glider is moveably related to the plunger.

Various objects and advantages of this invention will become apparent to those skilled in the art from the following detailed description of the preferred embodiment, when read in light of the accompanying drawings.

DETAILED DESCRIPTION OF THE INVENTION

Figure 1:
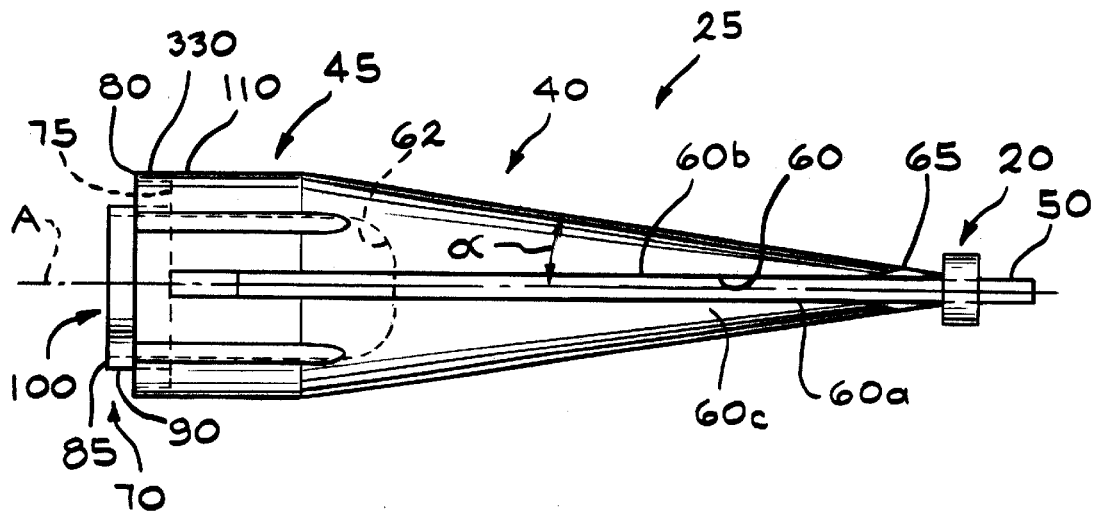
FIG. 1 is a elevation view of a serrated cone and ligature ring according to the invention.

Preliminarily, it should be noted that certain terms used herein, such as "upper", "lower", "top", "bottom", "distal", "proximal", "clockwise", "counterclockwise", "front", "back", and "side", are used to facilitate the description of the preferred embodiment of the invention. Unless otherwise specified or made apparent by the context of the discussion, such terms should be interpreted with reference to the figure under discussion. The term "distal" should be taken to mean the portion of the component under discussion which is most distant from the surgical instrument onto which a ligature ring is being loaded when the components of the invention are oriented in the arrangement shown in FIG. 11. Similarly, the term "proximal" should be taken to mean the portion of the component under discussion which is normally closest to the surgical instrument onto which the ligature ring is being loaded when the components of the invention are oriented in the arrangement shown in FIG. 11. Such terms are not intended as a limitation on the position in which the components of the invention may be used. Indeed, it is contemplated that the components of the invention may be easily hand-held in any desired orientation for use.

The invention is an apparatus for expanding a conventional elastomeric band 20, such as a ligature ring. The invention includes two components, a serrated cone 25 and a loader 30. The elastomeric band 20 and a McGivney Hemorrhoidal Ligator 35 (MHL) may be used with the serrated cone 25 and loader 30 of an embodiment of the invention as shown and described.

Referring now to FIGS. 1, 2, 3, and 4 the serrated cone 25 is shown. A longitudinal axis "A" extends through the serrated cone 25. The serrated cone 25 has a conical ramp portion indicated generally at 40, and a cylindrical base portion indicated generally at 45. In the illustrated embodiment the serrated cone 25 is also provided with a distally protruding elongate tip portion 50.

The proximal end of the tip portion 50 has a square cross section. It extends distally from the distal, small diameter end of the ramp portion 40. The distal end of the tip portion 50 preferably has a square cross section of smaller area than the proximal end, with the tip portion 50 being slightly tapered between the proximal and distal ends thereof. It is contemplated that the serrated cone 25 may suitably be formed with a tip portion 50 which is not rod-like. For example, the tip portion 50 of the serrated cone 25 may merely be a distal, small-diameter end of the conical ramp portion 40.

The conical ramp portion 40 has a narrow distal end and a wider proximal end. The tip portion 50 is fixed to the distal end of the ramp portion 40, while the proximal end of the ramp portion 40 joins the base portion 45. The proximal end of the ramp portion 40 defines a central hollow region 62 near the wider end. The ramp portion 40 preferably forms an angle, $\alpha$, of about 8 to 20 degrees with the longitudinal axis "A". In a preferred embodiment, the ramp portion 40 is hollow between the proximal end of the tip portion 50 and the proximal end of the base portion 45. In a preferred embodiment, the ramp portion 40 includes four radially outward curved surfaces 55 spaced apart by four longitudinally extending gaps, or fin slots 60.

Each of the fins slots 60 is defined by the ramp portion 40 and preferably has three surfaces 60a, 60b, 60c. One of the surfaces is a radially inward bottom surface 60a of the slot. Each of the other two surfaces 60b, 60c are generally radially extending parallel surfaces. The parallel surfaces 60b, 60c are spaced apart by a predetermined distance. Each of the parallel surfaces 60b, 60c forms a respective angle with the radially inner surface 60a. In a preferred embodiment, each angle is 90 degrees. The radially inner bottom surface 60a of each fin slot 60 forms a co-planar continuous surface with the respective adjacent flat outer surface of the tip portion 50. The fin slots 60 extend axially along the entire length of the ramp portion 40, and extend into the distal end of the base portion 45. The fin slots 60 formed in the serrated cone 25 preferably communicate with the central hollow region 62 of the ramp portion 40. At the distal end of the ramp portion 40, each fin slot 60 is preferably provided with a flared portion 65 by making the included angle between the bottom surface 60a of the slot and each of the other fin slot 60 surfaces 60b, 60c greater than 90 degrees. The purpose of the flared portion 65 will be described below.

The base portion 45 is a cylinder coaxial with the longitudinal axis "A". The base portion 45 has a proximal axial face 70. An annular groove 75 is defined in the axial face 70 of the base portion 45. A proximally extending circumferential flange 80 on the base portion 45 forms a radially outer surface 90 of the annular groove 75. Centrally disposed on the axial face 70 is a proximally extending cylinder 85. The cylinder 85 has a radially outer surface 90 which forms a radially inner surface of the annular groove 75. The bottom of the annular groove 75, between the flange 80 and the proximally extending cylinder 85 is a generally flat surface perpendicular to the longitudinal axis "A". The surface forms a tool seat 95, the function of which shall be discussed below. The cylinder 85 extends proximally further from the tool seat 95, than does the flange 80. Preferably, a longitudinally extending bore 100 is formed in the center of the proximally extending cylinder 85. The longitudinal bore 100 extends through the base portion 45 into the central hollow region 62 of the ramp portion 40. In a preferred embodiment, four inwardly ramped surfaces 105 are formed at the proximal end of the fin slots 60. The inwardly ramped surfaces 105 extend between a radially outer surface 110 of the base portion 45 and the inner surface defining the radially outer surface 90 of the longitudinal bore 100. The inwardly ramped surfaces 105 form an angle of about 45 degrees with the longitudinal axis "A".

Four grooves, or pin slots 115, extend parallel to the longitudinal axis "A" from the axial face of the base portion 45 to meet the sloped curved surfaces 55 of the proximal portion of the ramp portion 40. In a preferred embodiment, the number of degrees between each pin slot 115 is determined by dividing the number of fin slots 60 into 360 degrees. In a preferred embodiment having four pin slots 115, the pin slots 115 are at 90 degrees to each other.

Figure 5:
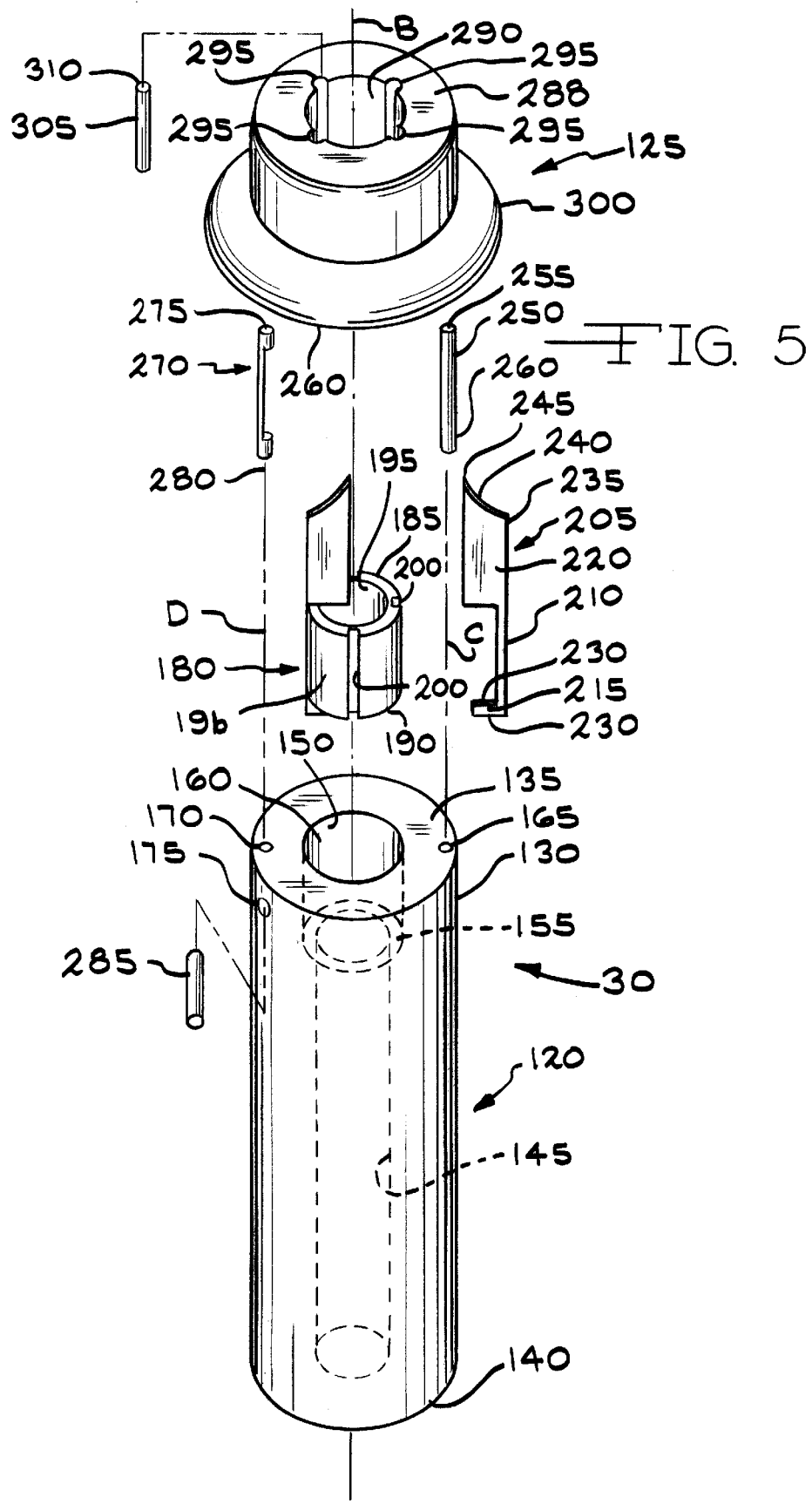
FIG. 5 is a top view in perspective of two fins, a fin ring, and a plunger.
Figure 6:
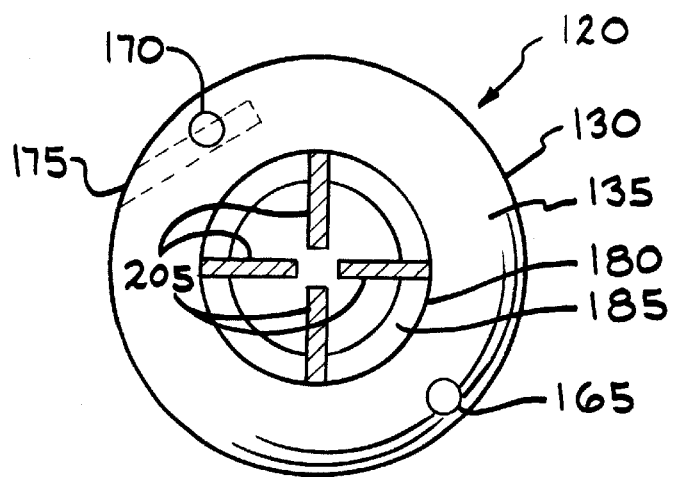
FIG. 6 is a cross section view of the fins and plunger.

Referring now to FIGS. 5 and 6, the loader 30 is shown having a plunger 120 that is moveably associated with a glider 125 in a way and for a purpose to be described below. The plunger 120 is a hollow cylinder, preferably metal, having a generally smooth radially outer surface 130, a generally smooth proximal axial face 135, and generally smooth distal axial face 140. The radially outer surface 130 may be textured or otherwise structured for ease of handing and use. A small bore 145 is formed centrally through the distal end of the plunger 120 along a longitudinal axis "B" of the plunger 120. A large bore 150 is formed centrally through the plunger 120 along the longitudinal axis "B". The large bore 150 communicates with the small bore 145. A radially extending shoulder is defined between the large bore 150 and the small bore 145. The radially extending shoulder is a fin seat 155, the purpose of which will be discussed below. The radially inward surface of the large bore 150, together with the fin seat 155, define a fin ring receptacle 160, the purpose of which will be discussed below.

The proximal axial face 135 of the plunger 120 defines a glider rod receptacle 165, and diametrically opposite from the glider rod receptacle 165, a retention rod receptacle 170, the purpose of which will be discussed below. The glider rod receptacle 165 and the retention rod receptacle 170 are bores having, respectively, a longitudinal axis "C" and a longitudinal axis "D" extending parallel to the longitudinal axis "B". A bore 175 is formed in the plunger 120 which is skew to the longitudinal axis "B" and the longitudinal axis "D." The bore 175 extends from the radially outer surface 130 of the plunger 120 to communicate with the retention rod receptacle 170.

An annular fin ring 180 is disposed in the fin ring receptacle 160. The fin ring 180 is preferable made of metal. The fin ring 180 has a proximal axial face 185 and a distal axial face 190. The distal axial face 190 is spaced apart from the fin seat 155. The fin ring 180 has an outer diameter enabling it to be press fit into the fin ring receptacle 160. The fin ring 180 has a longitudinally extending bore 195 therethrough which is preferably approximately the same diameter as the small bore 145 in the plunger 120.

A radially outward surface 196 of the fin ring 180 defines a plurality of longitudinally extending notches 200, four notches 200 in a preferred embodiment. The notches 200 extend from the proximal axial face 185 to the distal axial face 190. In a preferred embodiment, the proximal axial face 185 of the fin ring 180 is flush with the proximal axial face 135 of the plunger 120. Preferably the fin ring 180 is press-fit into the fin ring receptacle 160, so that the radially outer surface 196 of the fin ring 180 engages a longitudinally extending surface 150 of the fin ring receptacle 160 to hold the fin ring 180 in place. Of course, various other methods could be used to fix the fin ring 180 in place, such as pinning the fin ring 180 in place.

A preferred embodiment of the loader 30 employs four fins 205. Only two of the four fins 205 are shown in FIG. 5 for clarity. Fins 205 are preferably made of metal. Each fin 205 is a flat plate with a notch formed in an inward portion thereof, leaving a fin leg 210. Distal of the fin leg 210 is a radially inward extending fin foot 215, while proximal of the fin leg 210 is a fin body 220. The height of each fin leg 210 is approximately the same as the longitudinal length of the fin ring 180. Each fin leg 210 is disposed in a respective notch in the fin ring 180. The distal-most surface 225 of the fin foot 215 is seated against the fin seat 155. The proximal-most surface 230 of the fin foot 215 engages the distal face of the fin ring 180. The fin ring 180 holds the fin foot 215 in contact with the fin seat 155. The fin body 220 shares a radially outward edge 235 with the fin leg 210 and fin foot 215. The fin body 220 defines a fin cap 240. The fin cap 240 is an arcuate notch formed in the fin 205 to form a concave proximal surface thereof, with the upper portion tapering from the radially outward edge 235 to a radially inward proximal point 245.

The loader 30 further includes a cylindrical glider rod 250. A proximal end 255 of the glider rod 250 is permanently joined to the distal axial face 260 of the glider 125. A distal end 265 of the glider rod 250 is slideably disposed in the glider rod receptacle 165. The glider rod 250 is guided for movement along the axis "C."

A retention rod 270 is a cylinder that defines an inwardly disposed notch in a middle portion thereof. A proximal axial face 275 of the retention rod 270 is permanently joined to the distal axial face 260 of the glider 125. The retention rod 270 is preferably disposed at an approximately 180 degree angle to the glider rod 250. The distal end 280 of the retention rod 270 is slideable in the retention rod receptacle 170. The retention rod 270 is thus guided for movement along the axis "D."

A retention pin 285 is preferably press-fit into the plunger 120. The retention pin 285 is generally horizontally disposed through the radially outer surface of the plunger 120, preferably parallel to the proximal axial face of the plunger 120. The retention pin 285 fills a retention rod receptacle 170 to cooperate with the inwardly disposed notch of the retention rod 270. The retention rod 270 communicates with the retention rod receptacle 170 and is prevented from uncoupling therewith by the retention pin 285. The glider 125 of the loader 30 is generally cylindrical and disposed adjacent to the proximal axial face of the plunger 120. The glider 125 proximal axial face 288 preferably has a diameter about equal to the diameter of the plunger 120. The glider 125 has a bore 290 formed therethrough. The glider bore 290 diameter is preferably about equal to the diameter of the fin ring 180. In a preferred embodiment, the bore 290 defines four longitudinally disposed grooves 295. The grooves 295 preferably extend radially through an angle of greater than 180 degrees. The lower portion of the glider 125 forms a radially extending glider flange 300. The diameter of the glider flange 300 is preferably greater than the diameter of the plunger 120.

Figure 7:
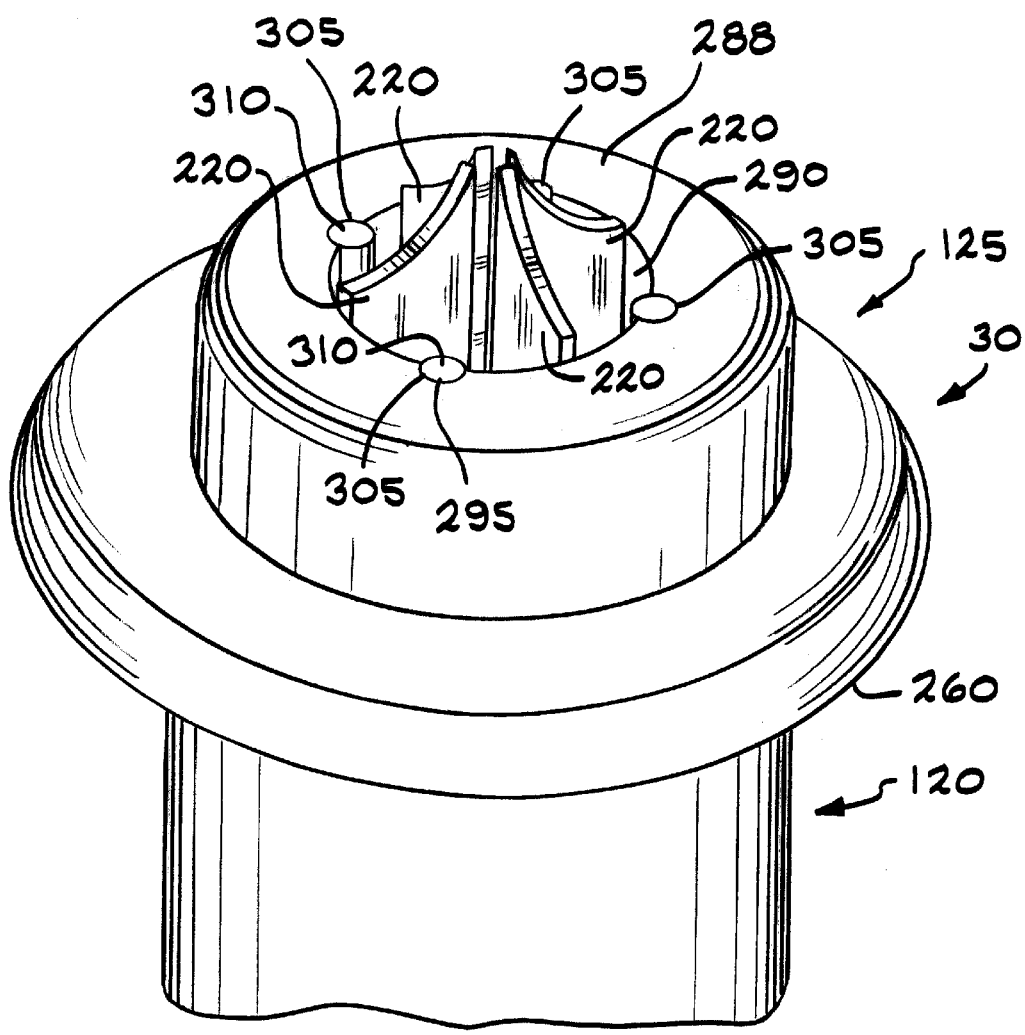
FIG. 7 is a top view in perspective of the plunger with the glider in a retracted position.

Referring now to FIG. 7, the plunger 120 is shown with the glider 125 in a retracted position. The glider 125 is in a retracted position when the distal axial face 260 of the glider 125 engages the proximal axial face 135 of the plunger 120. In the retracted position, the glider 125 may also engage the proximal axial face 185 of the fin ring 180 (FIG. 5). In the retracted position, the proximal portion of each fin body 220 extends through the glider bore 290 to protrude out of the proximal end of glider bore 290.

One or more longitudinally extending band pusher pins 305 are housed in the longitudinally extending grooves 295 of the glider 125. A preferred embodiment includes four cylindrical band pusher pins 305. In a preferred embodiment, the band pusher pins 305 are radially disposed at 90 degrees to each other. In viewing FIG. 7, it will be appreciated that the proximal axial faces 310 of the band pusher pins 305 are preferably flush with the glider proximal axial face 288.

Figure 8:
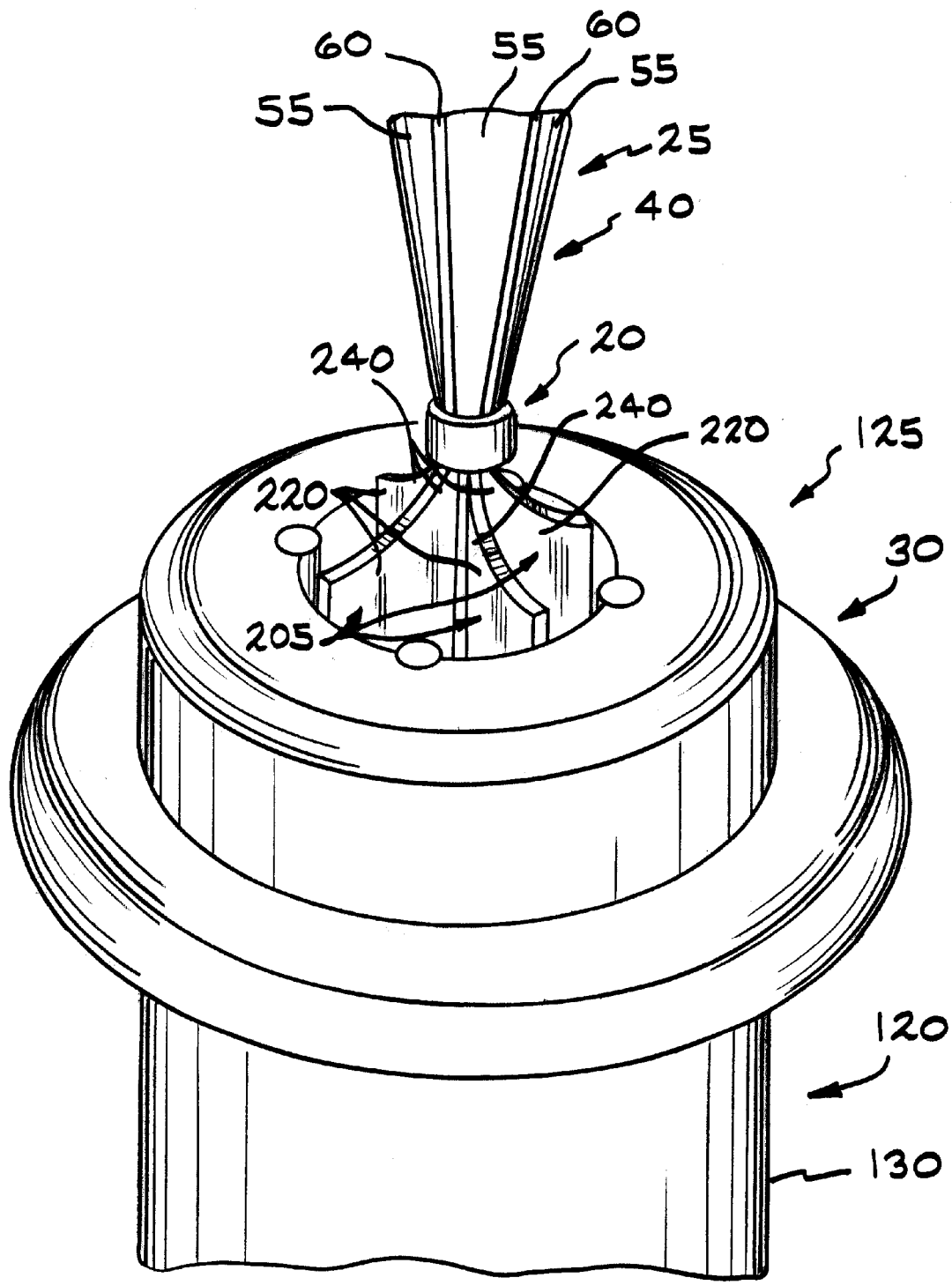
FIG. 8 is a top view in perspective of the plunger with the glider in a retracted position with the serrated cone inserted and ligature ring mounted on the serrated cone.

It will be appreciated that FIGS. 1, 8, 9, 10, and 11 are a series of views showing the interactivity between the elastomeric band 20, serrated cone 25, and loader 30. The serrated cone 25, and the loader 30 are shown axially aligned. For FIGS. 8, 9, and 10, the glider 125 is in a retracted position. In the retracted position, the fin caps 240 and proximal portion of each fin body 220 protrude proximally through the glider bore 290. In operation, the invention is simple and efficient. An elastomeric band 20 to be expanded and loaded onto a MHL 35 is first slipped onto the tip portion 50 of the serrated cone 25, as shown in FIG. 1. The elastomeric band 20 is well known in the art. It is an elastic ring, commonly rubber. It has an proximal axial face and a distal axial face. It has a radially outer surface and a radially inner surface. At rest, the inner diameter of the elastomeric band 20 is within the range of from about 0.4 millimeter to about 0.5 millimeter. Next, the serrated cone 25 is axially aligned with the loader 30 and the tip portion 50 of the serrated cone 25 is advanced between the proximal ends of the fins 205 of the loader 30, as shown in FIG. 8.

Referring now to FIG. 8, the elastomeric band 20 is shown engaged with the distal end of the ramp portion 40 of the serrated cone 25. The elastomeric band 20 is slightly distended due to a simultaneous engagement with the radially outward sloped proximal surfaces of the fins 205 of the loader 30. The proximal ends of the fin caps 240 are aligned with and partially inserted into respective ends of the fin slots 60. The flared portions 65 (FIGS. 1 and 2) of the fin slots 60 facilitate alignment of the fins 205 with the fin slots 60.

Figure 9:
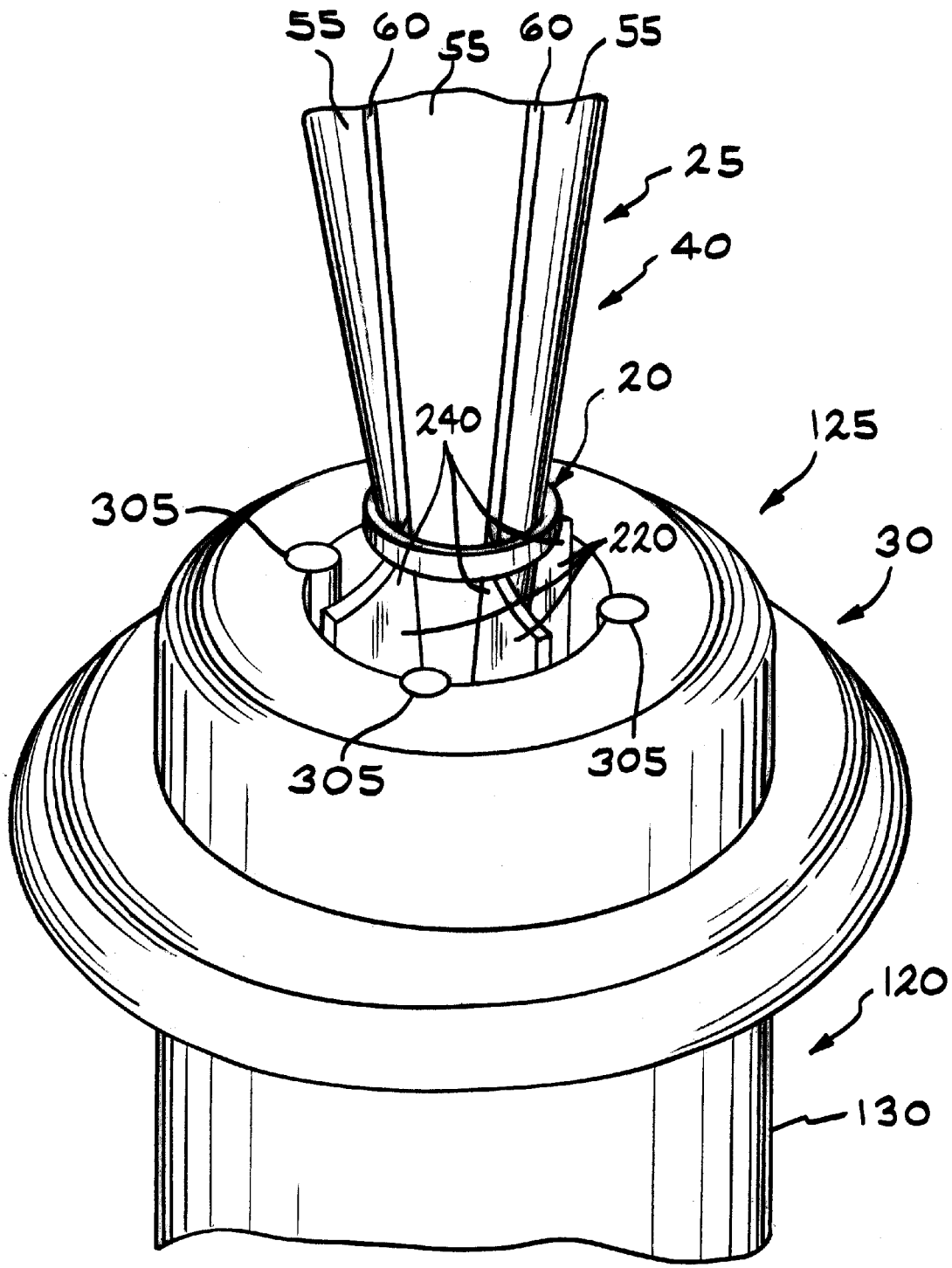
FIG. 9 is a top view in perspective of the plunger with the glider in a retracted position, serrated cone in partially-inserted position, and ligature ring in partially-stretched position.
Figure 10:
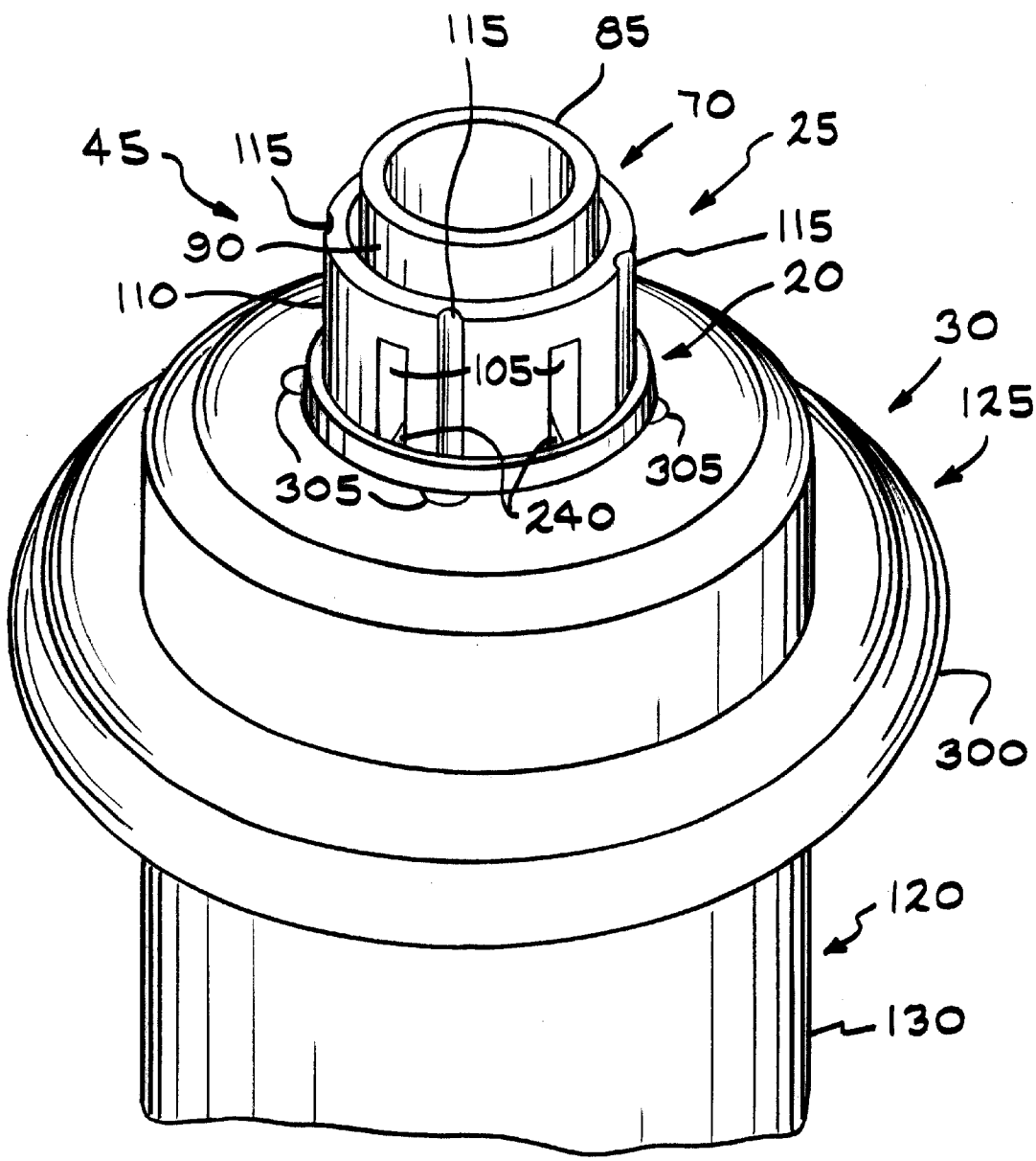
FIG. 10 is a top view in perspective of the plunger with the glider in a retracted position with a serrated cone in fully-inserted position and ligature ring in fully-stretched position.

Referring now to FIG. 9 the user urges the serrated cone 25 and the loader 30 relatively together causing the serrated cone 25 to move distally within the glider bore 290 compared to its position of FIG. 8. The elastomeric band 20 is forced to engage ever larger diameter proximal parts of the ramp portion 40 and ever wider, more radially outward portion of the fin caps 240, causing the elastomeric band 20 to be more distended. As the elastomeric band 20 becomes more distended, it also thins. The elastomeric band 20 is prevented from being pinched and damaged in the small annular gap between the glider 125 and the radially outer surface 110 of the base portion 45 (as seen in FIG. 10) of the serrated cone 25 during subsequent proximal movement of the glider 125 by the radially inwardly extending band pusher pins 305 of the glider 125, which will engage the elastomeric band 20 which will engage the elastomeric band 20 and prevent the glider 125 from overriding the elastomeric band 20. Of course, other arrangements may be made to prevent overriding the elastomeric band 20 including for example, radially inwardly extending fins 205 formed integrally with the glider 125 extending into the pin slots 115 (as seen in FIG. 10) or similar slots on the serrated cone 25.

Figure 11:
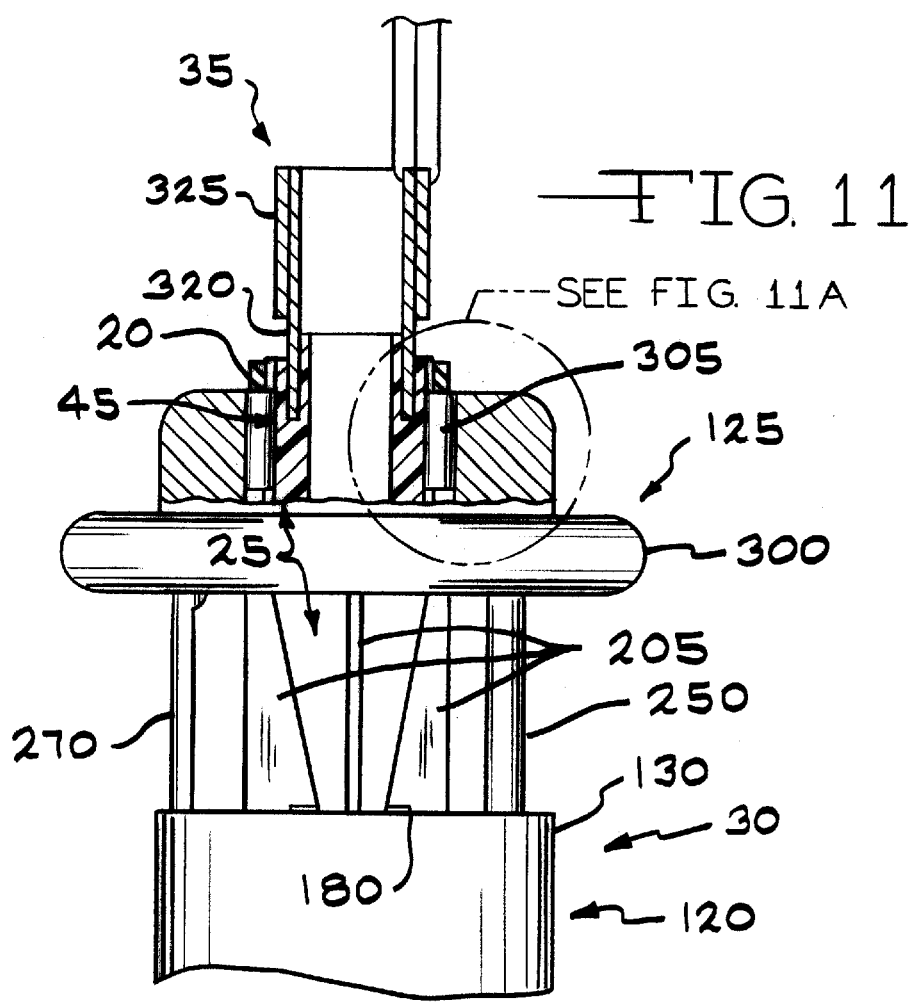
FIG. 11 is a side view of the plunger with the glider in partially extended position, a serrated cone inserted and a ligature ring in fully-stretched position and MHL seated.
Figure 12:
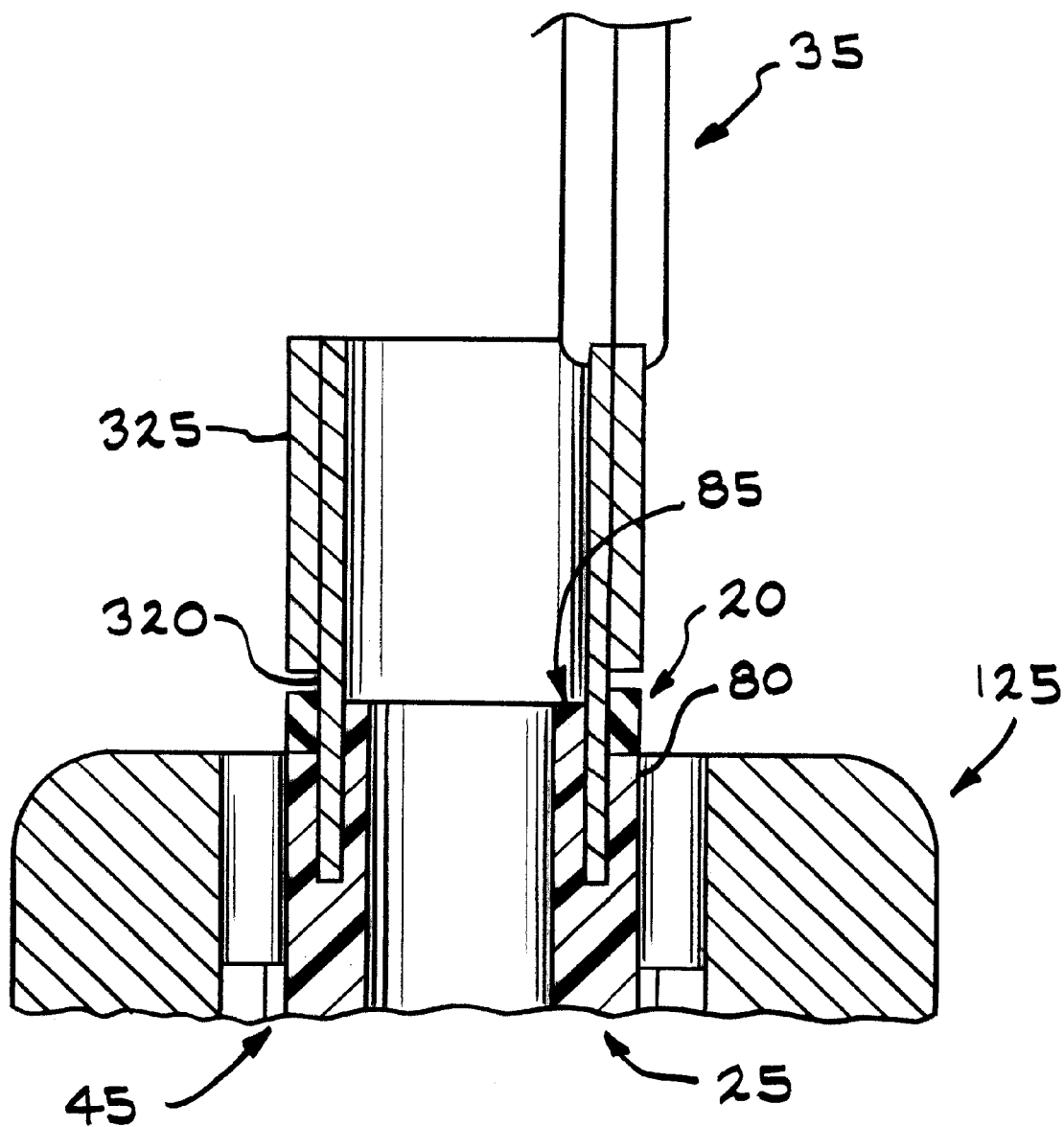
FIG. 12 is a side view of the plunger with the glider in partially extended position with a serrated cone inserted and ligature ring on the MHL.

As the serrated cone 25 and loader 30 are further advanced toward one another, the elastomeric band 20 is moved by the fins 205 of the loader 30 onto the base portion 45 of the serrated cone 25. Simultaneously, the band pusher pins 305 engage the pin slots 115. It will be appreciated that the elastomeric band 20 is more distended compared to FIGS. 8 and 9. After the serrated cone 25 is fully urged into the loader 30 as seen in FIG. 10, the user inserts an MHL 35 or similar device into the annular groove 75 of the base portion 45 of the serrated cone 25, as shown in FIGS. 11 and 12.

The MHL 35 is well known in the art. It includes a proximal handle portion (not shown) which supports a regulated distally extending sleeve assembly 315. The handle portion is shaped to accommodate the human hand. A proximal portion of the handle engages the palm of the hand. A distal portion of the handle engages the fingers of the hand. The sleeve assembly 315 includes an inner cylindrical sleeve 320 and an outer cylindrical sleeve 325. The inner sleeve 320 and the outer sleeve 325 form a close slip fit with one another.

Figure 2:
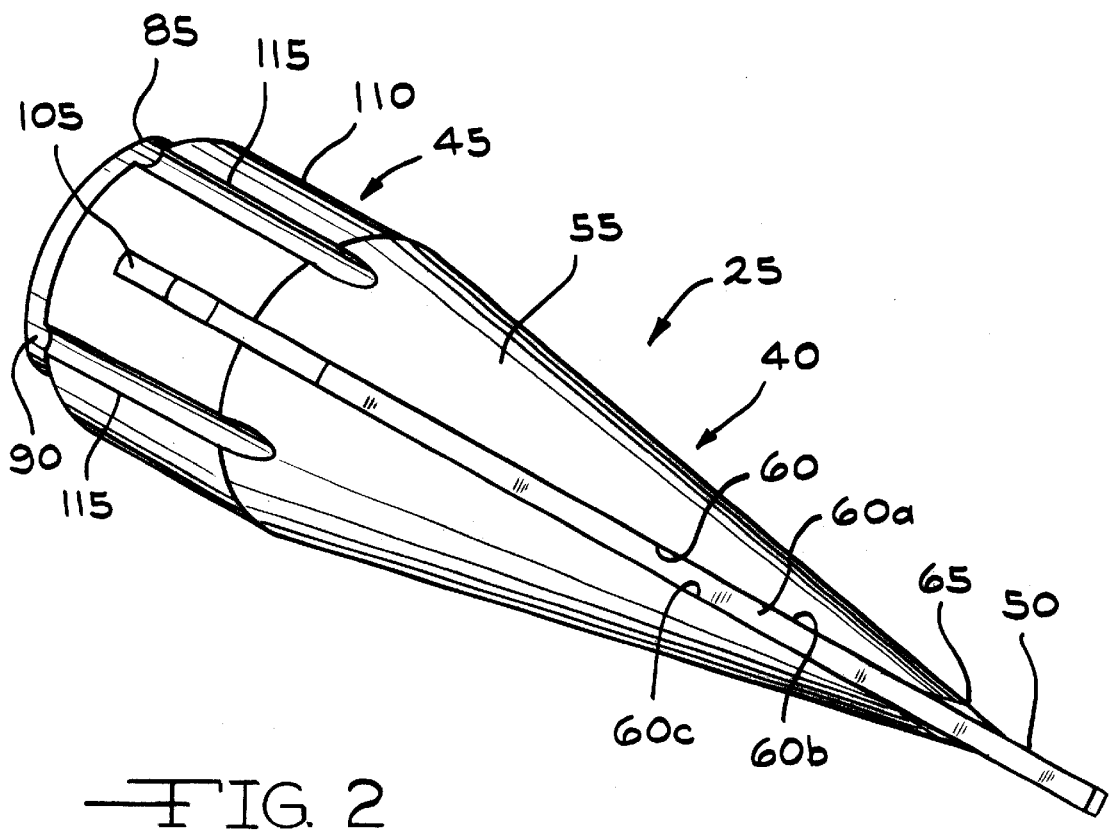
FIG. 2 is a top view in perspective of the serrated cone and ligature ring of FIG. 1.
Figure 3:
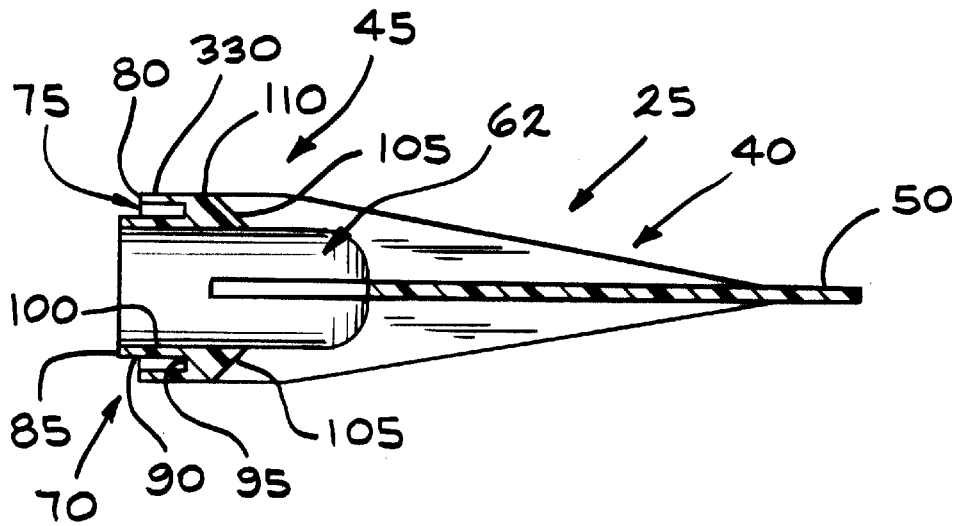
FIG. 3 is a cross section view of the serrated cone of FIG. 1.
Figure 4:
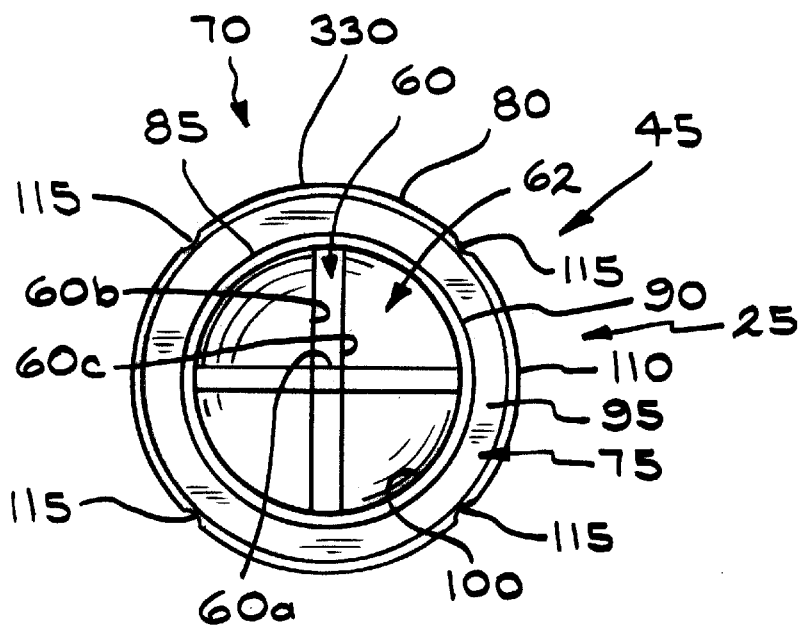
FIG. 4 is a bottom view of the serrated cone of FIG. 1.

In the illustrated embodiment, the MHL 35 engages an inner surface 330 of the proximally extending flange 80 of the base portion 45 with a friction fit, to help retain the MHL 35 and serrated cone 25 in their joined condition. However, the MHL 35 may alternatively or also form a friction fit with the proximally extending cylinder 85 of the base portion 45. Indeed, as will be discussed below, other structures for frictionally joining the MHL 35 and serrated cone 25 are contemplated. It is also contemplated that the serrated cone 25 may be joined to a modified MHL 35 through other means, such as a bayonet-type lock between an MHL 35 having an L-shaped groove or slot formed in the inner sleeve thereof (FIGS. 13 and 14) and a cooperating lug formed on either the radially inner surface 330 of the proximally extending flange 80 of the serrated cone 25 or the radially outer surface 90 of the proximally extending cylinder 85 of the cone 25 (FIGS. 1 and 2).

Figure 11A:
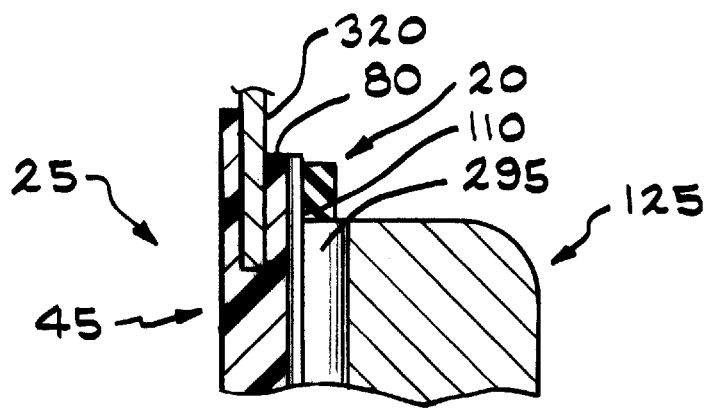
FIG. 11A is an enlarged view of the section 11A of FIG. 11, but showing the band pusher pin removed for clarity.

The elastomeric band 20 is displaced proximally from its position in FIG. 10 by displacing the glider 125 proximally. The glider 125 is most conveniently displaced proximally by the operator's pushing against the distal axial face 260 of the glider flange 300. It will be appreciated that the band pusher pins 305 engage the distal portion of the elastomeric band 20 to prevent the elastomeric band 20 from rolling and being overridden by the glider 125 as discussed above. Additionally at least the radially outer portion of the distal axial face of the elastomeric band 20 is in contact with the proximal axial face of the glider 125, urging the elastomeric band 20 proximally over the radially outer surface 110 of the base portion 45 of the serrated cone 25 as shown in FIG. 11A.

When mated with the tool seat 95 in the annular groove 75 of the base portion 45 of the serrated cone 25, the inner sleeve 320 of the MHL 35 is radially inward of the proximally extending circumferential flange 80 on the cone base portion 45. As the glider 125 is moved so that the proximal face of the glider 125 is aligned with the proximal end of the circumferential flange 80, the elastomeric band 20 is displaced proximally from the cone base portion 45 and contracts to engage the inner sleeve 320 of the MHL 35. The user then disengages the MHL 35 from the tool seat 95, then used according to the art to displace the elastomeric band 20 from the MHL 35 onto the base of the hemorrhoid to be treated.

Alternate embodiments of the serrated cone 25 are contemplated. The serrated cone 25 can be made of metal, for example stainless steel. The serrated cone 25 can be generally solid. The solid serrated cone 25 (FIGS. 1 and 2) will not include the longitudinally extending bore formed through the base portion 45 on the central a hollow region 62 of the ramp portion 40. The solid cone may be more reusable than a hollow cone since it may be easier to sterilize. The solid cone might also have a greater weight than the hollow cone which some surgeons and surgical assistants may prefer.

The serrated cone 25 can also be fitted with one or more attachments, such as a spring to facilitate the temporary joining of the MHL 35 and the serrated cone 25. The attachment could be disposed about the radially outer surface of the proximally extending cylinder 85, the radially inner surface of the proximally extending circumferential flange 80, or both. The attachment could also be disposed about the tool seat 95. The purpose of the attachment would be to help retain the MHL 35 against the tool seat 95. The attachment would promote reliable displacement of the elastomeric band 20 from the cone base portion 45 to the inner sleeve 320 of the ME 35. The attachment would also prevent or reduce lateral movement of the cone and the MHL 35 with respect to each other. Preferably the attachment would permit the cone to accommodate MHL's of varying diameters.

Figure 13:
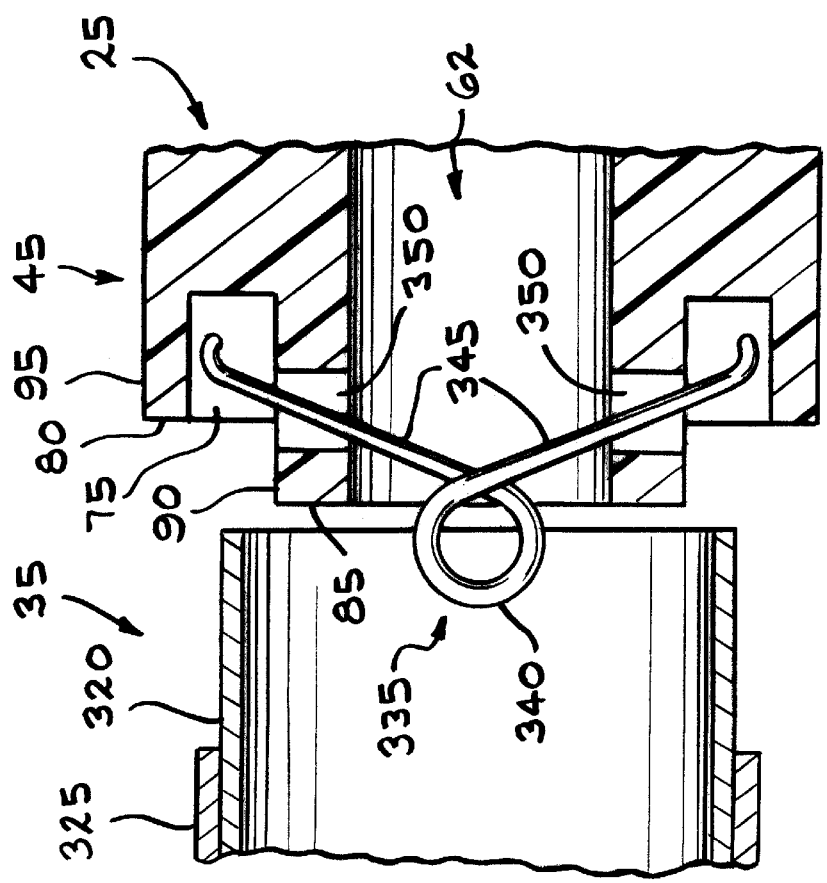
FIG. 13 is an alternate embodiment of the serrated cone including a spring in a relaxed position.

Referring now to FIG. 13 an alternate embodiment of the serrated cone 25 including a spring 335 is shown. The spring 335 is shown in a relaxed position. The spring 335 includes a longitudinally extending proximal head portion 340 and two radially extending leg portions 345. The spring 335 is preferably metal, but can be made of any suitable material.

In this embodiment, the proximally extending cylinder 85 of the base portion 45 defines two opposed spring gaps 350. A respective leg portion 345 of the spring 335 extends radially through an associated one of the spring gaps 350 into the annular groove 75 defined in the axial face 70 of the base portion 45. The head portion 340 is preferably centrally disposed within the proximally extending cylinder 85.

Figure 14:
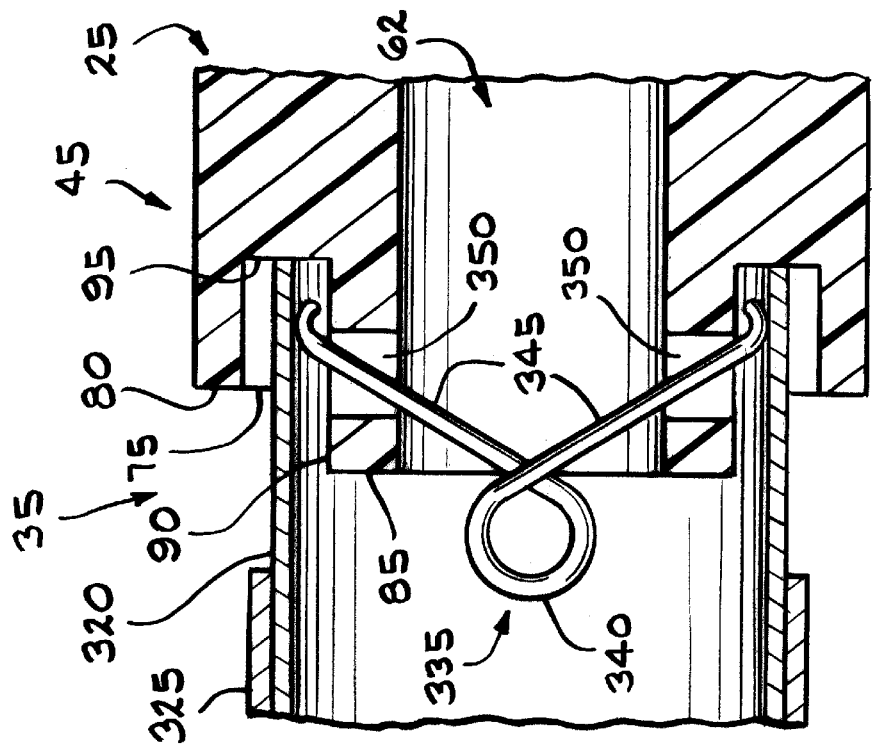
FIG. 14 is an alternate embodiment of the serrated cone including a spring in a flexed position.

Referring now to FIG. 14 the spring 335 is shown in a flexed position. The radially outer surfaces of the spring leg portions 345 contact the radially inner surface of the MHL 35 inner sleeve 320. It will be seen that the spring leg portions 345 illustrated in FIG. 14 are flexed radially inwardly compared to the spring leg portions 345 shown in FIG. 13. The spring head portion 340 is more proximally disposed than to the head portion 340 shown in FIG. 13. The inner sleeve 320 of the MHL 35 is thus frictionally held in contact with the tool seat 95. It will be appreciated that this arrangement will provided secure frictional engagement between the serrated cone 25 and MHL 35 inner sleeve's 320 of a variety of diameters.

The loader 30 can also be made and used with a longitudinally extending recess (not shown) in the radially outer surface 130 of the proximal portion of the plunger 120. The recess could be employed with or in place of the glider flange 300. The recess would provide a space for the operator of the invention to grip the distal portion of the plunger 120 during movement of the glider 125.

Figure 15:
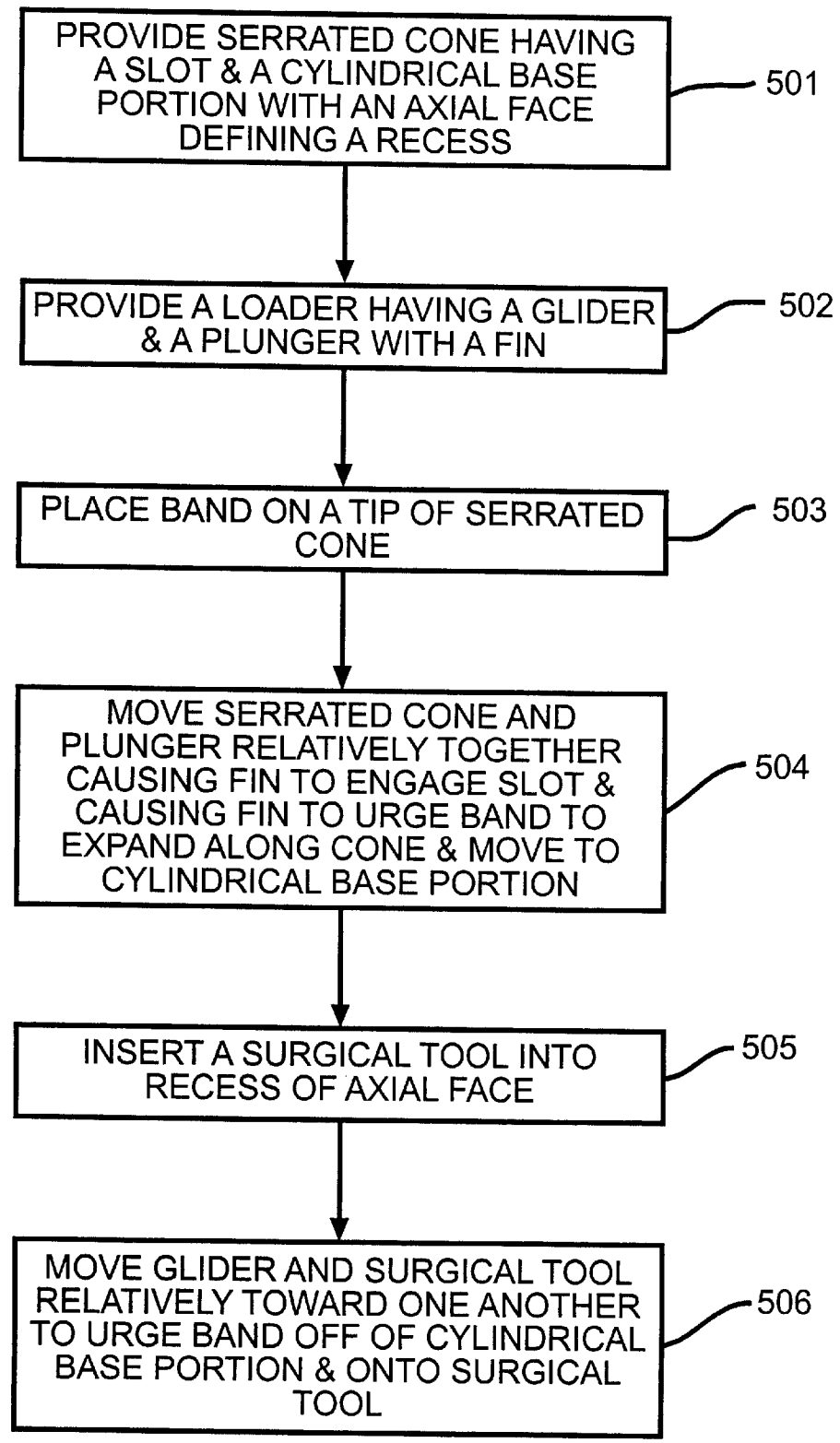
FIG. 15 is a flow chart illustrating a method of sketching an elastomeric band according to the invention.

FIG. 15 illustrates a summary of the forgoing explanation of the method of stretching an elastomeric band according to the invention. A first step 501 includes providing a serrated cone having a conical ramp portion and a cylindrical base portion, a longitudinally extending slot being formed in the ramp portion, and a tip portion. A second step 502 includes providing a loader having a plunger, a fin fixed to the plunger adapted to engage the slot, moveable relative to the plunger. A third step 503 includes placing an elastomeric band on the tip portion of the serrated cone. A fourth step 504 includes moving the serrated cone and the plunger relative toward one another so that the fin is moved into the slot of the serrated cone and the elastomeric band is moveable engaged by the fin to urge the elastomeric band from the tip portion to the base portion of the serrated cone. A fifth step 505 and sixth step 506 may be performed if the loader provided in the second step 502 further includes a glider mounted on the plunger for reciprocating movement relative thereto, and the base portion is provided with an axial face and a recess formed in the axial face. The fifth step includes placing a surgical tool into the recess of the cone base portion. The sixth step 506 includes moving the glider and the surgical tool relatively toward one another to cause the glider to engage the elastomeric band and urge the elastomeric band from the base portion onto the surgical tool.

The principle and mode of operation of this invention have been described in its preferred embodiments. However, it should be noted that this invention may be practiced otherwise than as specifically illustrated and described without departing from its scope.

For example, the elastomeric rings can be made of rubber or any other suitable material. Indeed, the exact materials for the rings elastomeric rings can vary with the use and desired properties of the elastomeric rings. The elastomeric rings can be used in conjunction with a wide variety of instruments, including but not limited to medical and dental instruments. Likewise, the serrated cone and loader of the invention can be used in conjunction with a wide variety of instruments, including but not limited to medical and dental instruments. The serrated cone and loader of the invention can be made from a wide variety of materials depending upon their use and performance requirements.

What is claimed is:

1. An apparatus for loading an elastomeric band comprising:
   a) a cone, said cone including:
      i. a conical ramp portion defining a cone ramp surface and having a large diameter end and a small diameter end;
      ii. a cylindrical base portion extending longitudinally from said large diameter end of said conical portion, said base portion having a radially outer surface;
      iii. at least one fin slot defined in said cone ramp surface and said radially outer surface of said base portion; and
   b) a loader, said loader including:
      i. a plunger having a fin for urging said elastomeric band along said conical ramp portion; and
      ii. a glider having a surface for engaging said elastomeric band and urging said elastomeric band over said base portion, said glider being moveably related to said plunger.

2. The apparatus of claim 1 wherein said fin includes an arcuate notch formed therein to form a concave proximal surface thereof.

3. The apparatus of claim 1 wherein said fin is retained in said plunger by a ring centrally disposed within said plunger.

4. The apparatus of claim 1 wherein said fin is capable of being receivably mated with said cone and said elastomeric band.

5. The apparatus of claim 1 further comprising an elongate glider rod axially aligned with said plunger.

6. The apparatus of claim 1 further comprising a retention rod axially aligned with said plunger, wherein said glider is movably retained to said plunger by said retention rod.

7. The apparatus of claim 1 wherein said glider has a radially outwardly extending flange.

8. The apparatus of claim 1 wherein said cone further comprising an elongated tip portion.

9. The apparatus of claim 1 wherein said cone further comprising a pin slot extending from an axial face of the base portion to meet a sloped outer surface of a proximal portion of the ramp portion.

10. The apparatus of claim 1, wherein said fin slot includes a flared portion formed in said small diameter end of said conical portion.

11. The apparatus of claim 10, wherein said flared portion of said fin slot is defined by a bottom wall and a side wall of said fin slot, said bottom wall and said side wall meeting at an angle greater than ninety degrees within said flared portion of said fin slot.

12. The apparatus of claim 1, wherein said cylindrical base portion defines an inwardly ramped surface at a proximal end of said fin slot.

13. A method of expanding elastomeric bands comprising:
   a) providing a serrated cone having a conical ramp portion and a cylindrical base portion, a longitudinally extending slot being formed in said ramp portion, and a tip portion;
   b) providing a loader having a plunger, a fin fixed to said plunger adapted to engage said slot, moveable relative to said plunger;
   c) placing an elastomeric band on said tip portion of the serrated cone; and
   d) moving said serrated cone and said plunger relative toward one another so that said fin is moved into said slot of said serrated cone and said elastomeric band is moveable engaged by said fin to urge said elastomeric band from said tip portion to said base portion of said serrated cone.

14. The method of claim 13 wherein said loader further includes a glider mounted on said plunger for reciprocating movement relative thereto, and wherein said base portion is provided with an axial face and a recess formed in said axial face, further including the steps of:
   e) placing a surgical tool into said recess of said cone base portion; and
   f) moving said glider and said surgical tool relatively toward one another to cause said glider to engage said elastomeric band and urge said elastomeric band from said base portion onto said surgical tool.

15. An apparatus for moving an elastomeric band over a serrated cone conical ramp portion and a cylindrical base portion comprising:
   a. a plunger having a fin for urging said band along said conical ramp portion, said plunger being a bored cylinder and said fin being retained in said plunger by a cylindrical ring centrally disposed within said plunger; and
   b. a glider having a surface for engaging said elastomeric band and urging said elastomeric band over said cylindrical base portion, said glider being movably related to said plunger.

16. A band loading cone comprising:
   a conical portion defining a cone ramp surface and having a large diameter end and a small diameter end;
   a cylindrical base portion extending longitudinally from said large diameter end of said conical portion, said base portion having a radially outer surface; and
   at least one fin slot defined in said cone ramp surface and said radially outer surface of said base portion, said fin slot including a flared portion formed in said small diameter end of said conical portion.

17. A band loading cone comprising:

a conical portion defining a cone ramp surface and having a large diameter end and a small diameter end;

a cylindrical base portion extending longitudinally from said large diameter end of said conical portion, said base portion having a radially outer surface; and at least one fin slot defined in said cone ramp surface and said radially outer surface of said base portion said cylindrical base portion defining an inwardly ramped surface at a proximal end of said fin slot.

* * * * *